(12) United States Patent
de Francisco Martin et al.

(10) Patent No.: US 10,886,509 B2
(45) Date of Patent: Jan. 5, 2021

(54) BATTERY OPERATED DEVICE AND BATTERY REMOVAL METHOD

(71) Applicant: Stichting IMEC Nederland, Eindhoven (NL)

(72) Inventors: Ruben de Francisco Martin, Eindhoven (NL); Marianne Anne Marie Vandecasteele, Eindhoven (NL); Victor Van Acht, Veldhoven (NL)

(73) Assignee: Stichting IMEC Nederland, Eindhoven (NL)

( * ) Notice: Subject to any disclaimer, the term of this patent is extended or adjusted under 35 U.S.C. 154(b) by 552 days.

(21) Appl. No.: 15/159,320

(22) Filed: May 19, 2016

(65) Prior Publication Data
US 2016/0359150 A1  Dec. 8, 2016

(30) Foreign Application Priority Data

Jun. 4, 2015  (EP) .................................... 15170714

(51) Int. Cl.
*A61B 5/04* (2006.01)
*H01M 2/10* (2006.01)
(Continued)

(52) U.S. Cl.
CPC ............. *H01M 2/1038* (2013.01); *A61B 5/01* (2013.01); *A61B 5/0408* (2013.01);
(Continued)

(58) Field of Classification Search
CPC ........ A61N 1/0492; A61N 1/08; A61N 1/048; A61N 1/3702; A61N 1/04;
(Continued)

(56) References Cited

U.S. PATENT DOCUMENTS 4,487,820 A * 12/1984 Engelstein ............. H05K 3/301
429/1
5,188,912 A *  2/1993 Katoh ................. H01M 2/1044
429/100
(Continued)

FOREIGN PATENT DOCUMENTS

EP    2 465 415 A1    6/2012
GB    2487758 A    8/2012
(Continued)

OTHER PUBLICATIONS

European Search Report, European Patent Application No. 15170714.8 dated Nov. 26, 2015.

*Primary Examiner* — Joseph A Stoklosa
*Assistant Examiner* — Brian M Antiskay
(74) *Attorney, Agent, or Firm* — McDonnell Boehnen Hulbert & Berghoff LLP

(57) ABSTRACT

A battery operated device and method of removing a battery therefrom are described. The battery operated device includes a battery compartment, a battery in the battery compartment, and an electric component powered by the battery. The battery compartment is mounted on a deformable base and includes a top surface which is adapted to be ruptured by deforming the deformable base, thereby enabling removal of the battery from the battery compartment. The method of removing a battery from a battery compartment of a battery operated device includes rupturing a top surface of the battery compartment by deforming a deformable base of the battery compartment, and removing the battery from the battery compartment.

17 Claims, 4 Drawing Sheets

(51) Int. Cl.
*H01M 6/52* (2006.01)
*A61B 5/01* (2006.01)
*A61B 5/0408* (2006.01)
*A61B 5/00* (2006.01)
*H01M 6/02* (2006.01)
*H01M 10/54* (2006.01)

(52) U.S. Cl.
CPC ......... *A61B 5/4266* (2013.01); *H01M 2/1022* (2013.01); *H01M 2/1044* (2013.01); *H01M 6/02* (2013.01); *H01M 6/52* (2013.01); *H01M 10/54* (2013.01); *H01M 2220/30* (2013.01); *Y02W 30/84* (2015.05)

(58) Field of Classification Search
CPC .......... Y10T 29/49117; G08B 21/0453; G01N 27/307; A61B 5/04085; A61B 5/0006; A61B 2560/0412; A61B 5/6833; A61B 5/04087; A61B 5/0402; A61B 5/02438; A61B 5/6832
USPC ................. 600/372, 382, 384–393, 508–509
See application file for complete search history.

(56) References Cited

U.S. PATENT DOCUMENTS

| | | | |
|---|---|---|---|
| 5,203,455 A | 4/1993 | Hewelt et al. | |
| 5,948,006 A | 9/1999 | Mann | |
| 6,144,749 A | 11/2000 | Fideler | |
| 6,456,872 B1* | 9/2002 | Faisandier | A61B 5/04085 600/390 |
| 7,981,535 B2* | 7/2011 | Scott | H01M 2/1044 429/100 |
| 2008/0275327 A1* | 11/2008 | Faarbaek | A61B 5/0002 600/382 |
| 2009/0024044 A1* | 1/2009 | Virtanen | A61B 5/0205 600/509 |
| 2011/0144470 A1* | 6/2011 | Mazar | A61B 5/04085 600/391 |
| 2013/0285681 A1 | 10/2013 | Wilson et al. | |
| 2013/0317333 A1* | 11/2013 | Yang | A61B 5/00 600/372 |
| 2014/0031663 A1* | 1/2014 | Gallego | A61B 5/04085 600/386 |
| 2014/0100432 A1* | 4/2014 | Golda | A61B 5/04325 600/301 |
| 2014/0121557 A1* | 5/2014 | Gannon | A61B 5/002 600/549 |
| 2014/0206977 A1* | 7/2014 | Bahney | A61B 5/6833 600/391 |
| 2015/0087951 A1* | 3/2015 | Felix | A61B 5/04085 600/382 |
| 2015/0094558 A1* | 4/2015 | Russell | A61B 5/688 600/391 |
| 2015/0238094 A1* | 8/2015 | Lai | A61B 5/0002 600/301 |
| 2015/0250422 A1* | 9/2015 | Bay | A61B 5/6833 600/391 |

FOREIGN PATENT DOCUMENTS

| | | |
|---|---|---|
| WO | 2009/036348 A1 | 3/2009 |
| WO | 2015/056027 A1 | 4/2015 |

* cited by examiner though a rechargeable battery can be used if preferred,

BATTERY OPERATED DEVICE AND BATTERY REMOVAL METHOD

CROSS-REFERENCE TO RELATED APPLICATIONS

The present application is a non-provisional patent application claiming priority to European Patent Application No. EP 15170714.8, filed Jun. 4, 2015, the contents of which are hereby incorporated by reference.

FIELD OF THE DISCLOSURE

This present disclosure relates to the field of battery operated devices, and in particular devices which are disposable after use.

BACKGROUND

There are numerous examples of battery operated devices. When a device wears out, is broken, or has served its purpose and needs to be discarded (e.g. for hygienic reasons), it is typically necessary to remove the battery for separate disposal and recycling. Indeed, there are regulations which require proper disposal of batteries.

The proper disposal of the battery requires the battery to be removed from its battery compartment, and this can be an inconvenience for users, or it may even be difficult for users as a result of their poor eyesight or poor manual dexterity. Typically, a battery compartment has a screw closure or a slidable cover, and when the closure or cover is removed, the battery needs to be pried out of its compartment. Each of these operations can present difficulties for some users, and some designs may require the use of tools.

One example of a disposable device is a device for ambulatory monitoring of vital signs (such as ECG, etc.). In such devices, electrodes may be integrated into a single disposable patch, on which a re-usable electronic module can be clipped. In some cases, the electronic module has a rechargeable battery that has to be re-charged by the user prior to applying it on a patch. Alternatively, a non-rechargeable (called "primary") battery can be inserted in the electronic module.

In a hospital environment, non-rechargeable batteries are preferred over rechargeable batteries because of the handling required to keep rechargeable batteries charged when not in use, and reliability issues of rechargeable batteries after many times of use.

A problem with using non-rechargeable batteries in this application is the additional handling which is required by the user. First, the user must insert a fresh battery in the electronic module, and second the user must attach the electronic module to the patch. There is then the disposal issue already mentioned above after the disposable device has been used.

One proposal is to integrate a primary battery in the patch with the electrodes. In this way, it is guaranteed that with every patch a fresh battery is also applied, and only one initial action is required by the user, namely attaching the electronic module to the patch with its integrated battery.

The patch is intended to be used only by one user, for hygienic reasons. When disposing of the patch with its integrated battery, the battery thus still needs to be separated from the patch with the electrodes so it can be disposed of properly.

This is just one example of a battery operated device which presents inconvenience to a user in disposing of the battery. There are numerous other examples, where a device is only intended to be used for a short duration (possible even shorter than the life of the battery) and which therefore requires the battery to be disposed of by the user more often than in a device which is at least used until the battery is fully drained.

There is therefore a need for a design which enables easy removal of a battery from a battery operated device.

SUMMARY

According to an aspect, there is provided a battery operated device, comprising: a battery compartment; a battery in the battery compartment; and an electric component powered by the battery, wherein the battery compartment is mounted on a deformable base and comprises a top surface which is adapted to be ruptured by deforming the deformable base, thereby enabling removal of the battery from the battery compartment.

This device enables removal of the battery by deforming the bottom of the battery compartment, for example by pushing the battery out of the top of the battery compartment by pushing from beneath. This operation is for example analogous to removing a drug capsule from a blister package. Note that the top of the battery compartment may be at the top of the overall device, but equally it may be at the bottom of the overall device. Thus, the "top" of the battery compartment is to be understood as meaning an exposed face of the battery compartment, beneath which lies the battery.

The device may comprise: a deformable plastic substrate; a battery receiving location having an upwardly facing electrical contact for contacting a lower contact of the battery; and a rupturable foil arrangement over the battery which forms the top surface, having a downwardly facing electrical contact for contacting an upper contact of the battery.

The blister-type package thus incorporates electrical contacts for contacting the top and bottom faces of the battery. The flexible foil for example has a conducting layer, such as an aluminium foil layer, for contacting the battery, and it may additionally have an insulating cover layer so that the outside of the device is electrically insulated.

The deformable plastic substrate may comprise a PET foil.

The battery receiving location may comprise a locally thinner portion or locally removed portion of the deformable plastic substrate.

In such a scenario, the substrate does not all need to be sufficiently deformable to enable the battery to be removed. A local part may be thinner or removed. If there is a removed part of the substrate, there will be another layer beneath the substrate which supports the battery in the substrate opening. This other layer may be a metal foil which provides the electrical connection to the lower battery contact terminal.

Printed conductor tracks may be provided over the deformable plastic substrate for making electrical connection between the upwardly facing electrical contact and the electric component and between the downwardly facing electrical contact and the electric component.

These conductor tracks may be on one or both sides of the deformable plastic substrate.

The battery for example comprises a disk having electrical contacts at opposite ends of the disk. The battery may include a coin cell battery.

The battery is for example a non-rechargeable battery.

The device typically has an expected period of use which is equal to or shorter than the lifetime of the battery. In particular, as the device is damaged by removing the battery, it is not intended to reuse the device. There are many different devices which are for one use only. This may be for hygiene reasons for medical devices, or it may be because the device is expected to wear out before the battery expires, for example in a wearable application. For example, a monitoring device in a shoe may have a battery life which exceeds the expected life of the shoe itself.

In some examples, the device comprises a wearable health monitoring device. One such example is a patch for contact with the skin of a user. A specific example is an ECG monitoring patch.

In the case of a monitoring patch device, the device may comprise: a substrate with a patterned conductor arrangement on each side, the patterned conductor arrangement on one side defining patch electrodes and the patterned conductor arrangement on the other side defining electrical connector tracks, wherein: connection vias are provided through the substrate; or the patterned conductor arrangements together form a wrap-around layer which is foldable.

There are thus various options for making electrical connections to conductors on both sides of a substrate. The foldable design may fold over on itself, so that the substrate of the patterned conductor itself defines the overall device substrate. Alternatively, the foldable patterned conductor may be folded over an intermediate substrate.

Again in the case of a monitoring patch device, the device may comprise: a disposable patch part comprising: skin contact electrodes on one side of a deformable substrate, and the battery compartment on the opposite side of the deformable substrate; and an electrical connection port on the opposite side of the deformable substrate, wherein the electrical component comprises a re-usable electronics module which connects to the electrical connection port.

This provides a plug-in electronics module, which can be re-used after the patch is disposed of. The removal of the electronics module is a simple unplug operation and the removal of the battery for separate disposal is a simple blister pack type removal operation.

According to another aspect, there is provided a method of removing a battery from a battery compartment of a battery operated device, the method comprising: rupturing a top surface of the battery compartment by deforming a deformable base of the battery compartment, and removing the battery from the battery compartment.

This method gives a simple operation for a user to dispose of a battery correctly when use of the battery operated device is at an end.

A method of disposing of a battery operated device is also provided, comprising, at the end of use of the device, the end of use being at the end or before the end of the battery lifetime: removing the battery using the method as defined above; and separately disposing of the device and the battery.

BRIEF DESCRIPTION OF THE FIGURES

Example embodiments will now be described in detail, with reference to the accompanying drawings, in which.

DETAILED DESCRIPTION

There is provided a battery operated device in which a battery is provided in a battery compartment with a top surface which can be ruptured by deforming the base of the compartment, to enable removal of the battery from the battery compartment. In this way, a battery is provided in a blister pack type enclosure. This enables easy removal of the battery for suitable disposal.

Figure 1:
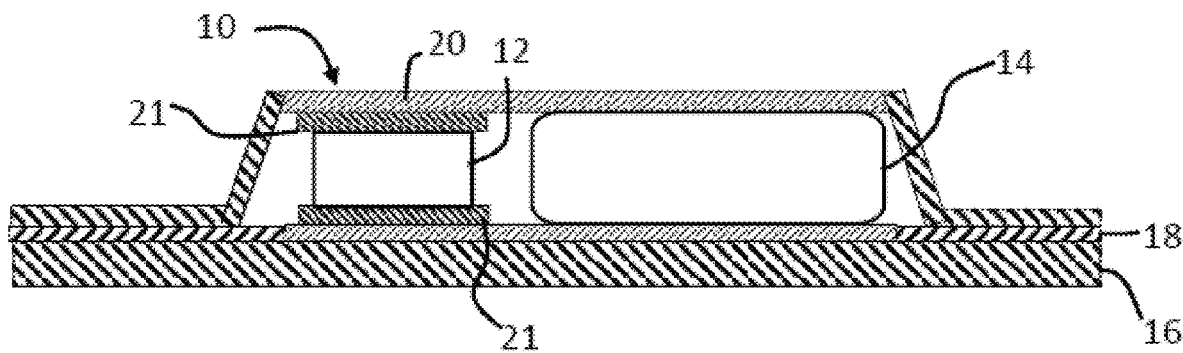
FIG. 1 illustrates an electrical device according to an example embodiment.

FIG. 1 shows a general device according to an embodiment of the invention. The device comprises a battery compartment 10 with a battery 12 in the battery compartment. An electric component 14 is powered by the battery. The battery for example comprises a disk having electrical contacts at opposite ends of the disk. In an example embodiment, the battery may include a non-rechargeable coin cell battery.

In this example, the device has a deformable substrate 16 for the whole of the device, and which itself defines a deformable base of the battery compartment 10. The substrate 16 has a conductor track arrangement shown as layer 18 which makes electrical connection between the bottom terminal of the battery 12 and a terminal of the component 14. This conductor arrangement 18 thus provides an upwardly facing electrical contact for contacting a lower contact of the battery 12.

The battery compartment 10 has a top surface 20 which can be ruptured by deforming the base. The top surface forms or includes a downwardly facing electrical contact for contacting an upper contact of the battery. The battery can then be removed from the battery compartment after rupturing the top surface. The top surface also provides electrical connection between the top terminal of the battery 12 and a (top) terminal of the component 14. As illustrated in FIG. 1, the top terminal of the battery and the component 14 can each be a ground terminal. For example, the top surface may include a metal foil, which may even be exposed to the outside. This may be an aluminum foil layer. It may however have additional insulating layers so that there is no external electrical contact.

FIG. 1 illustrates that the battery may include an optional conductive gel, conductive adhesive or glue, or sponge or spring or the like 21 on each terminal for improving the electrical contact.

This device enables removal of the battery 12 by deforming the bottom of the battery compartment, for example pushing the battery out of the top of the battery compartment by pushing from beneath. This operation is analogous to removing a drug capsule from a blister package.

The substrate 16 may be a deformable plastic, such as PET.

This general outline of the device structure applies to many different types of devices. However, the present battery/component structure may be specifically applied in devices which have an expected period of use which is equal to or shorter than the lifetime of the battery. Thus, at the end of the battery life, or before, the device has completed its function and is to be discarded. The device thus may be a disposable product. The device is damaged by removing the battery (by rupturing the top of the battery compartment), so it is not intended to be re-used.

Some more detailed examples will now be given, which relate to a wearable health monitoring device. One example of particular interest is a patch monitor for contact with the skin of a user, such as for ECG monitoring. Other skin contact devices may be included in the scope of the present application, such as those for sweat monitoring, for temperature monitoring, or detecting target chemicals.

Figure 2:
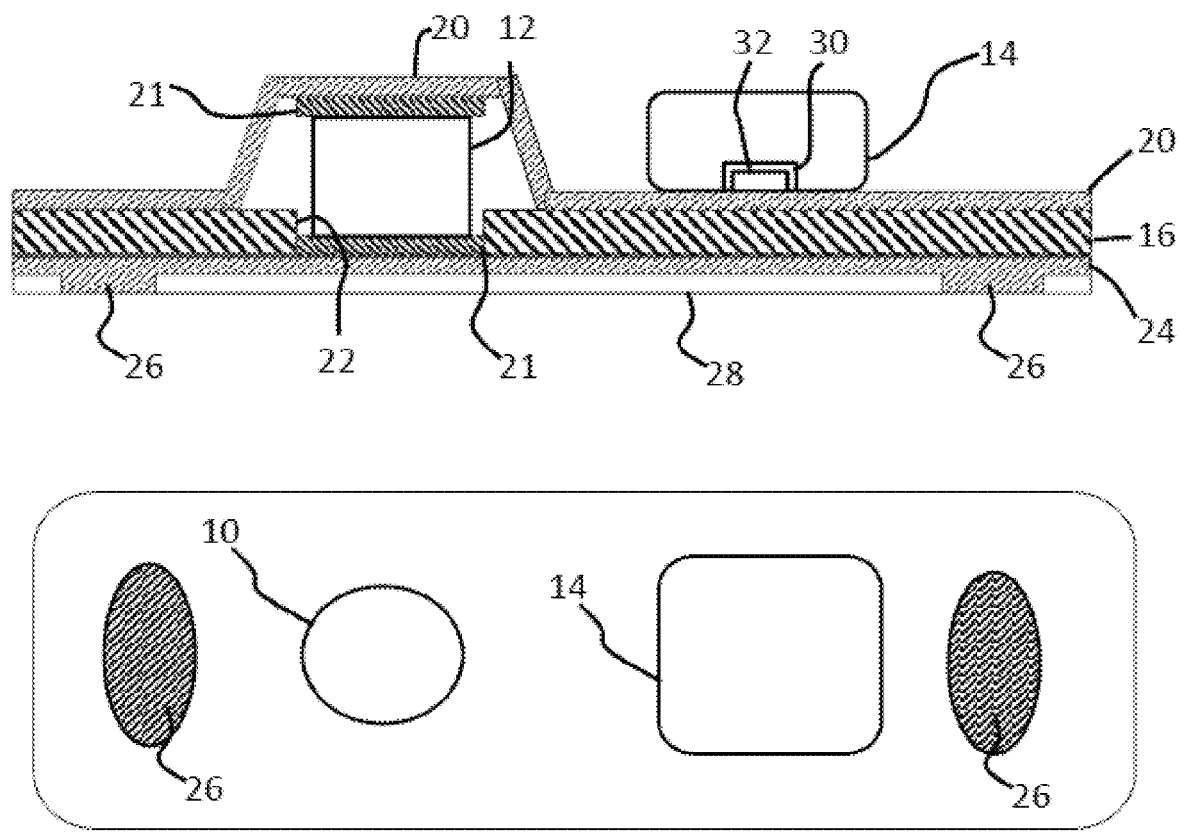
FIG. 2 illustrates a patch type medical monitoring device according to an example embodiment.

FIG. 2 shows an example of an ECG monitoring patch, in cross sectional view through the battery compartment, and in plan view.

The same components as in FIG. 1 are given the same reference numbers. In the example of FIG. 2, the battery is received in an opening 22 in the substrate 16. Beneath the PET substrate 16 is an electrode layer 24 which defines a set of patch electrodes 26. The electrode layer 24 is a metal foil which provides the electrical connection to the lower battery contact terminal. An insulating cover layer 28, such as silicone, covers the electrode tracks formed by layer 24 but leaves the patch electrodes 26 exposed.

The substrate 16 thus does not need to be sufficiently flexible to enable the battery to be removed, since this can be achieved based on the deformability of the portions of the layers 24 and 28 which define the base of the battery compartment 10. The substrate will instead have its properties selected for the desired ability to form the patch into a desired shape over the skin of the user. The substrate may have a local thinner part for the battery compartment rather than a removed part.

The connection between the lower electrode layer 24 and the electrical component 14 may be made through the substrate, or else the top and bottom electrode layers 20, 24 may be a single layer which wraps around the edge of the device, and thus provides all the required interconnections without requiring any vias.

The electrical tracks may be printed conductor tracks, either printed directly onto the substrate or else printed onto their own carrier layer which is then applied to the substrate. As is clear from the examples of FIGS. 1 and 2, conductor tracks may be on one or both sides of the deformable plastic substrate.

The example of FIG. 2 has a patterned conductor arrangement on each side of the substrate, with the lower side defining at least patch electrodes and the patterned conductor arrangement on top side defining electrical connector tracks.

As explained above, one design of ECG patch monitoring device may include a non-rechargeable battery and a re-usable electronics module. For this purpose, the electrical component 14 of FIG. 2 is implemented as an electronics module which has an electrical connector 30 which plugs into an electrical connection port 32. This may use a standard SD connector (as used in memory cards), although another suitable connector may be used.

Such a scenario provides a plug-in electronics module, which can be re-used after the patch is disposed of. The removal of the electronics module includes an unplug operation and the removal of the battery for separate disposal includes a blister pack type removal operation.

Figure 3:
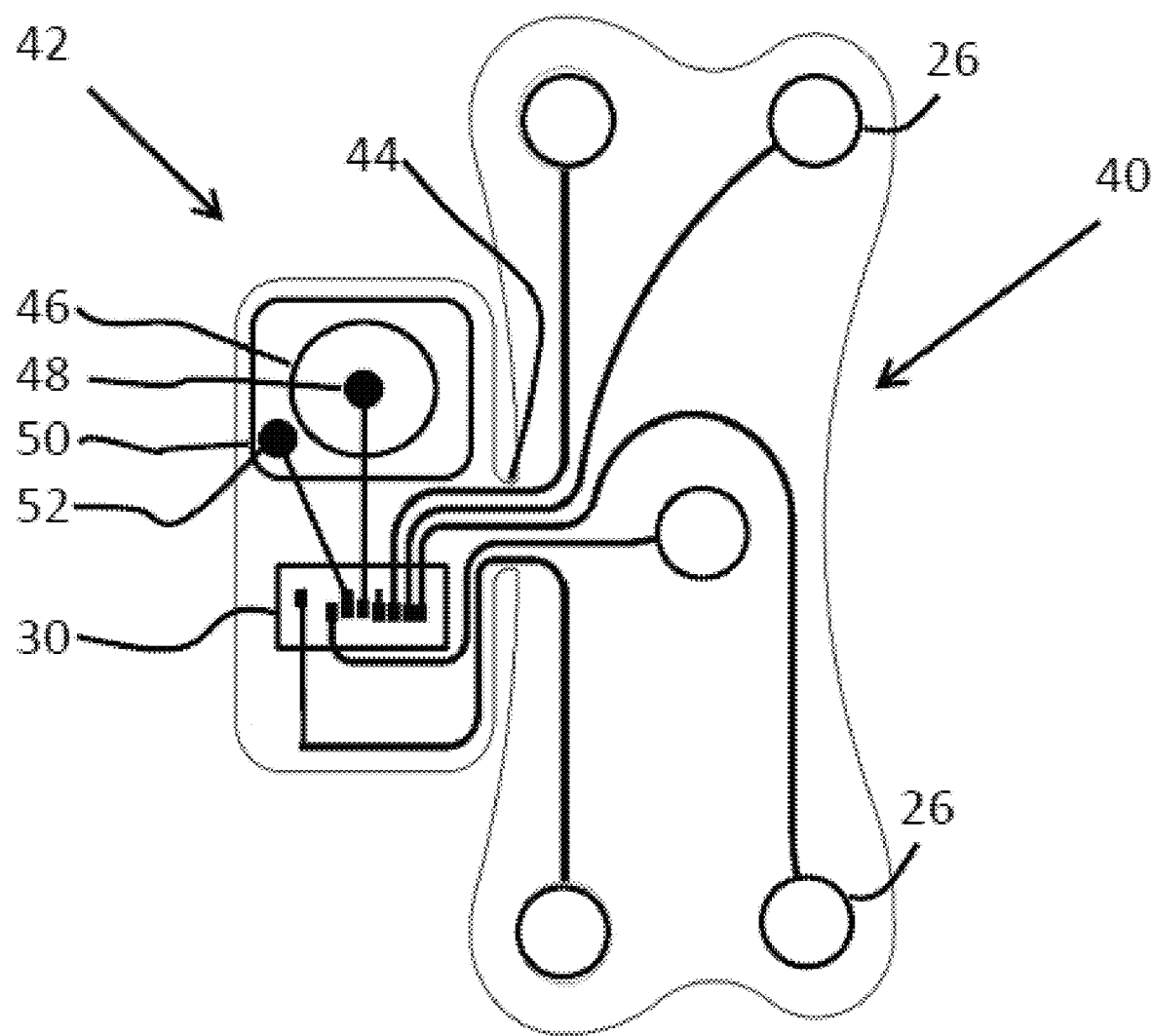
FIG. 3 shows an electrical connector arrangement according to an example embodiment.

FIG. 3 shows an example of a single layer structure used to form the patch electrodes and the electronic module connections. The layer may itself form the substrate 16 so that it is wrapped around on itself, or it may be wrapped around a separate substrate layer. The layer structure has a lower portion 40 and an upper portion 42, with a fold tab 44 between them. The lower portion 40 carries the patch electrodes 26 and the top portion 42 carries the external electrical connector 30 for receiving the electronics module 14.

In this example the battery receiving portion 46 is provided on the upper portion 42 and an electrical conductor 48 is routed to the base of the battery receiving portion. A foil cover part 50 is provided over the battery compartment, which makes contact to another electrical conductor 52. In this way, the top and bottom electrical contacts of the battery connect to the electric circuit. The layer structure is covered with an insulating layer, such as silicone, which only leaves exposed the battery contacts and the patch electrodes.

The single layer structure avoids the need to use vias to connect between opposite sides of the device. The conductive tracks may be printed on a PET base by screen printing silver ink. The ink is then cured, for example at a temperature of around 120 degrees Celsius. The electrodes 26 can be made by screen printing silver chloride ink and then curing. Finally the SD card holder (or other connector arrangement) 30 is mounted on the tracks as desired.

The battery is fitted and the cover foil 50 for the blister pack type battery compartment is then applied.

The encapsulation with silicone or other insulator may take place before or after forming the battery compartment. If the encapsulation is before applying the cover foil 50, then the electrodes 48, 25 are left exposed. If the encapsulation is applied after applying the cover foil, then the patch electrodes and the battery compartment top cover may be left exposed so that the battery compartment top cover remains easily ruptured.

Figure 4:
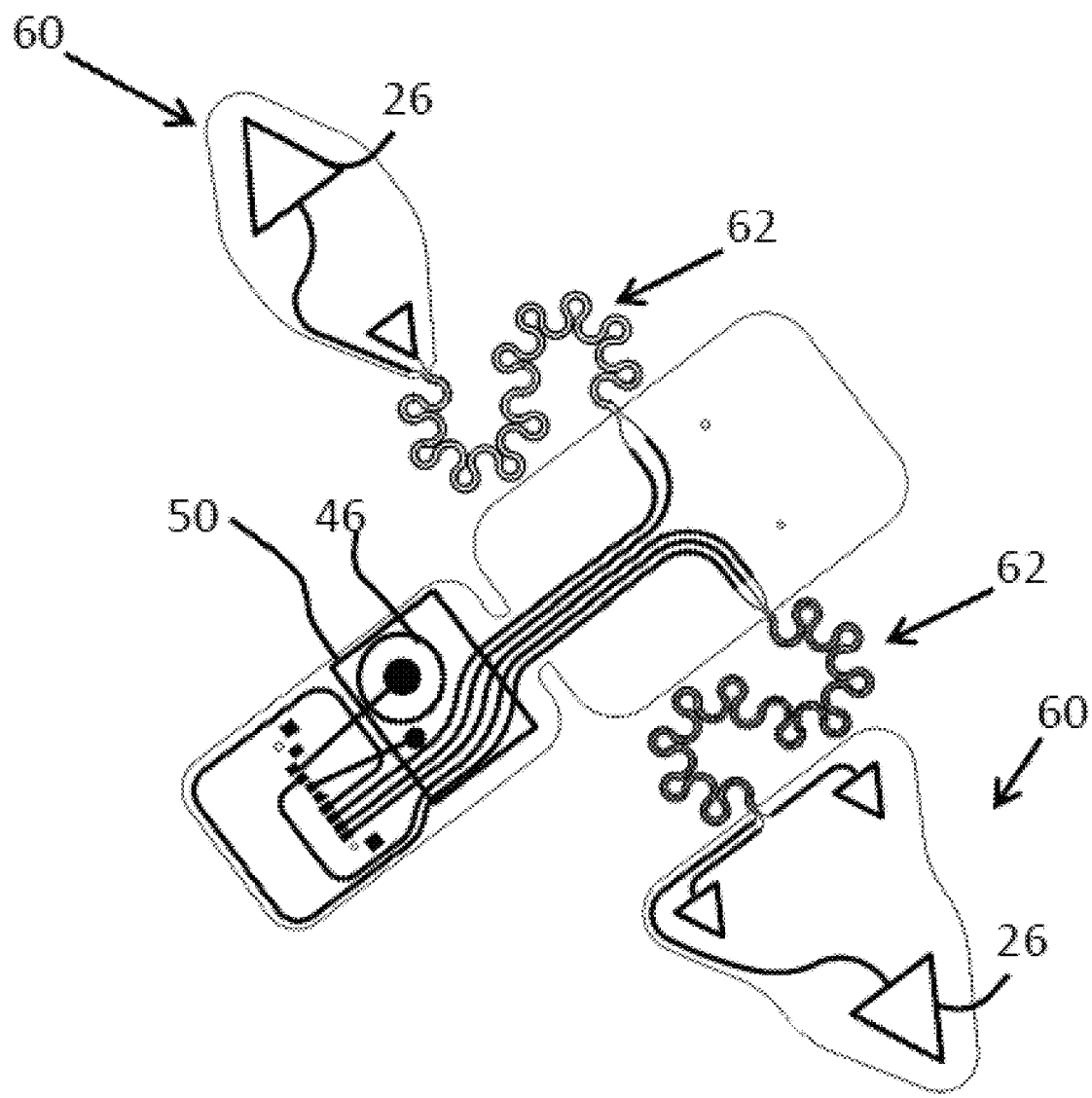
FIG. 4 shows an electrical connector arrangement according to an example embodiment.

FIG. 4 shows another similar foldable design in which patch electrodes regions 60 are separate from the main body so that they may be positioned more freely. They connect to the main body with flexible leads 62.

In order to remove the battery, the top surface of the battery compartment is ruptured by deforming the base of the battery compartment, and removing the battery from the battery compartment. This may be carried out as part of a method of disposing of the battery operated device at the end of use of the device. This end of use may be being at the end or before the end of the battery lifetime.

It will be understood from the description above that the invention can be applied to a variety of devices, and only detailed use has been described. There is a general need to dispose of batteries separately from other electrical components, so this invention is of interest for all disposable products, particularly, single use or limited time use products. The invention generally makes use of a blister pack type concept, and many different designs of conductor tracks and other electrical connections to the battery compartment will be apparent to those skilled in the art.

Various other modifications will be readily apparent to those skilled in the art. In the claims, the word "comprising" does not exclude other elements or steps, and the indefinite article "a" or "an" does not exclude a plurality. The mere fact that certain measures are recited in mutually different dependent claims does not indicate that a combination of these measured cannot be used to advantage. Any reference signs in the claims should not be construed as limiting the scope.

The invention claimed is:

1. A battery operated device, comprising: a battery compartment;
a battery in the battery compartment, wherein the battery comprises an upper contact and a lower contact, wherein at least one of the upper contact or the lower contact is coupled to the battery compartment by way of a conductive adhesive or a conductive gel;
an electric component powered by the battery, wherein the battery compartment is mounted on a deformable base where the deformable base comprises a top surface which is adapted to be ruptured, thereby enabling removal of the battery from the battery compartment;

a deformable plastic substrate with a first side and a second side opposite the first side, wherein the deformable plastic substrate comprises the deformable base, and wherein the deformable plastic substrate comprises an opening substantially surrounding the battery and the electric component;

a battery receiving location having an upwardly facing electrical contact for contacting a lower contact of the battery; and a flexible foil arrangement over the battery which forms the top surface, having a downwardly facing electrical contact for contacting an upper contact of the battery;

skin contact electrodes disposed on the first side of the deformable plastic substrate, and the battery compartment is disposed on the second side of the deformable plastic substrate.

2. The battery operated device of claim 1, wherein the deformable plastic substrate comprises a PET foil.

3. The battery operated device of claim 1, further comprising printed conductor tracks over the deformable plastic substrate for making electrical connection between the upwardly facing electrical contact and the electric component and between the downwardly facing electrical contact and the electric component.

4. The battery operated device of claim 1, wherein the battery comprises a disk having electrical contacts at opposite ends of the disk.

5. The battery operated device of claim 1, wherein the battery is a nonrechargeable battery.

6. The battery operated device of claim 1, wherein the battery operated device has an expected period of use which is equal to or shorter than a lifetime of the battery.

7. The battery operated device of claim 1, wherein the skin contact electrodes are configured to monitor electrocardiogram (ECG) signals.

8. The battery operated device of claim 6, further comprising:

a substrate with a patterned conductor arrangement on a first side and a second side, the patterned conductor arrangement on the first side defining skin contact electrodes and the patterned conductor arrangement on the second side defining electrical connector tracks, wherein: connection vias are provided through the substrate;

or the patterned conductor arrangements together form a wrap-around layer which is foldable.

9. The battery operated device of claim 8, further comprising an insulating layer, wherein the insulating layer covers at least a portion of the patterned conductor arrangement, wherein the insulating layer comprises silicone.

10. The battery operated device of claim 8, wherein the skin contact electrodes are coupled to the electric component via flexible leads, and wherein the skin contact electrodes are formed by screen printing and comprise silver chloride ink.

11. The battery operated device of claim 6, comprising: a disposable patch part comprising:

an electrical connection port on the second side of the deformable plastic substrate, wherein the electrical component comprises a re-usable electronics module which connects to the electrical connection port.

12. The battery operated device of claim 11, wherein the electrical connection port comprises a Secure Digital (SD) card connector.

13. A method of removing a battery from a battery compartment of the battery operated device of claim 1, the method comprising:

rupturing the top surface of the battery compartment by deforming the deformable base of the battery compartment, and removing the battery from the battery compartment.

14. The method of removing the battery from the battery compartment of the battery operated device of claim 13, wherein removing the battery from the battery compartment comprises separating the battery from the electric component previously powered by the battery.

15. A method of disposing of a battery operated device, comprising, at an end of use of the device, the end of use being at the end or before the end of a battery lifetime:

removing the battery using the method as claimed in claim 13; and separately disposing of the device and the battery.

16. The method of disposing of a battery operated device of claim 15 wherein separately disposing of the device and the battery is performed in accordance with local, state, or federal battery disposal laws.

17. The battery operated device of claim 8, further comprising a fold tab configured to facilitate a fold between the skin contact electrodes and the electrical component.

* * * * *